United States Patent [19]

Hrizo et al.

[11] 4,325,029
[45] Apr. 13, 1982

[54] ALKALI IONIZATION DETECTOR

[75] Inventors: John Hrizo, Monroeville; James E. Bauerle, Plum Borough; Robert E. Witkowski, West Mifflin, all of Pa.

[73] Assignee: Westinghouse Electric Corp., Pittsburgh, Pa.

[21] Appl. No.: 73,827

[22] Filed: Sep. 10, 1979

[51] Int. Cl.³ .................... G01N 27/62; G01R 35/00
[52] U.S. Cl. ..................................... 324/468; 324/74
[58] Field of Search ............. 324/464, 465, 466, 467, 324/468, 469, 470, 74, 130; 73/1 G, 1 R

[56] References Cited

U.S. PATENT DOCUMENTS 3,495,437  2/1970  Estes et al. ........................ 73/1 G
4,047,101  9/1977  Bauerle et al. ..................... 324/468
4,117,396  9/1978  Berkey et al. ...................... 324/468

Primary Examiner—Ernest F. Karlsen
Attorney, Agent, or Firm—M. P. Lynch

[57] ABSTRACT

A calibration filament containing a sodium-bearing compound is included in combination with the sensing filament and ion collector plate of a sodium ionization detector to permit periodic generation of sodium atoms for the in-situ calibration of the detector.

5 Claims, 3 Drawing Figures

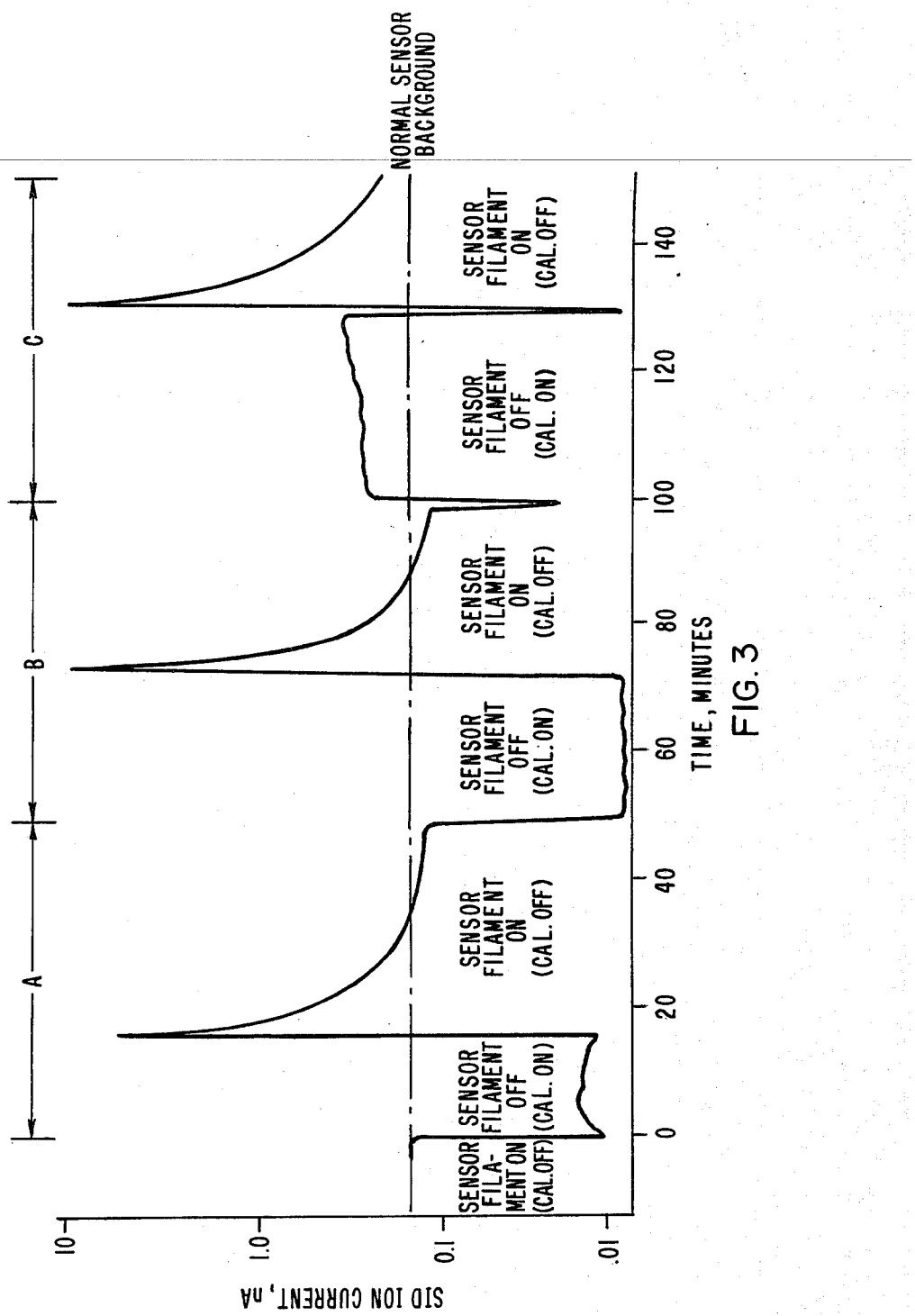

ALKALI IONIZATION DETECTOR

This invention resulted from work performed under the Department of Energy Contract No. EN-77-C-02-4197.

BACKGROUND OF THE INVENTION

The ability to detect and identify sodium leaks in an operating liquid metal fast breeder reactor is considered essential in preventing catastrophic failures from occurring. One commercially available instrument which meets this need is the Westinghouse Sodium Ionization Detector which is described in detail in U.S. Pat. Nos. 4,047,101, entitled, "Filament For Alkali Metal Ionization Detector", and 4,117,396, entitled, "Sensor For Thermally Ionizable Particles And/Or Vapors", both of which are assigned to the assignee of the present invention and incorporated herein by reference. Alkali ion sources are also described in an article entitled, "Duofilament Alkali Ion Source", American Journal of Physics, 47, 290 (1979).

Typically, the detectors are monitored in a control room which is remote from the breaker reactor facility. The detectors require removal from the reactor facility for periodic maintenance and calibration. The efficient use of the detectors could be significantly enhanced if a technique were provided for the in-situ calibration of the detector.

SUMMARY OF THE INVENTION

There is disclosed herein with reference to the accompanying drawings a modification to the ionization detector described in the above-referenced patent wherein a calibration filament is included in combination with the detector sensing filament and ion collector plate. The calibration filament contains a sodium-bearing compound that thermally volatizes the sodium as neutral sodium atoms in response to periodically applied electrical potential. The atoms thus generated deposit on the sensor filament and undergo the normal sequential operation of positive surface ionization consistent with the operation of the above-identified Westinghouse ionization detector. The ions are then attracted to the negatively charged collector plate thus resulting in a measurable current flow representative of the sodium generated by the calibrator filament. The calibrator filament may typically be operated with negative bias potential to suppress the emission of positive sodium ions which could produce a signal even if the sensor filament was not operative.

DESCRIPTION OF THE DRAWINGS

The invention will become more readily apparent from the following exemplary description in connection with the accompanying drawings:

FIGS. 2 and 3 are waveform illustrations of the operation of the detector illustrated in FIG. 1.

DESCRIPTION OF THE PREFERRED EMBODIMENT

While the following disclosure has general application to alkali metal ionization detectors operated in an oxygen-contained environment, the discussion for the purposes of clarity, will be directed in particular to a sodium ionization detector inasmuch as such a device is of particular current interest for monitoring sodium coolant systems such as those used in the fast breeder nuclear reactors.

Figure 1:
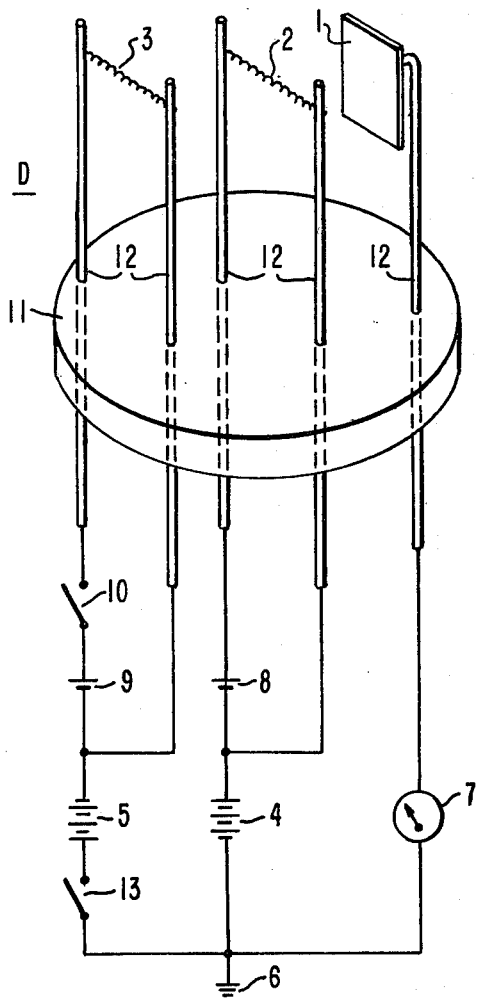
FIG. 1 is a sectioned schematic illustration of an ionization detector incorporating an in-situ calibrator filament.

The detector, as is typically illustrated in FIG. 1, employs a heated sensor filament, or thermal ionizer electrode, which responds to impinging sodium atoms or sodium containing atoms (vapor or aerosol) to form positive sodium ions which are attracted to an ion collector plate electrode via an electric field to produce an ion current which is an indication of the sodium concentration of the environment to which the heated sensor filament is exposed.

Referring to FIG. 1, a typical embodiment of an alkali metal ionization detector D is illustrated as consisting of a heated cathode sensor filament 2, also herein functionally referred to as a thermal ionizer electrode, an ion collector plate anode electrode 1, a filament transformer 16 for coupling the sensor filament voltage supply 8 to heat the sensor filament 2, an ion current meter 7 to indicate the ion current flow between the sensor filament 2 and the ion collector plate 1 which is maintained by an electric field produced by the voltage supply 4 which is connected between the sensor filament 2 and the ground terminal 6. This embodiment is described in the above-referenced U.S. patents.

Sodium particles, whether contained in a vapor, aerosol or sodium compound, transported by a carrier gas such as flowing air to the vicinity of the detector D are converted to free sodium ions at the surface of the heated sensor filament 2 which functions as a thermal ionizer. These ions are then collected by the ion collector plate 1 which is maintained at a negative potential relative to the heated sensor filament 2 by the voltage source 4. The flow of ions thus established produces an ion current which is measured by the ion current meter 7 as an indication of the concentration of sodium ions present in the environment adjacent to the heated sensor filament 2. The process by which the sodium particles are converted to free sodium ions can be thought of as occurring in the following steps:

(1) The collision of sodium particles with the surface of the heated sensor filament 2 and their subsequent melting;

(2) The rapid surface diffusion of the melted sodium over the heated sensor filament 2 to form a layer of adsorbed sodium atoms;

(3) The transfer of valence electrons from some of the adsorbed sodium atoms to the heated sensor filament 2, converting them to adsorb sodium ions; and (4) The desorption of the sodium ions from the surface to become free ions, as well as the desorption of neutral sodium ions.

The free sodium ions thus generated contribute to the ion current monitored by the ion current meter 7.

Additionally there is disclosed in combination with the sensor filament 2 and the ion collector plate 1, a calibration filament 3 which is supported within the detector D at a location adjacent to the sensor filament 2. A calibration filament power supply 9 is connected across the calibration filament 3 and a bias voltage source 5 is connected between the calibration filament 3 and the ground terminal 6. The periodic activation of the calibration filament 3 is operator controlled via a calibration switch 10 which is typically located in a remote control room. The filament power supply 9 functions to heat the calibration filament 3 such that upon activation of the calibration filament 3, which contains or is coated with a material comprising sodium bearing compounds, results in the volatilization of sodium atoms from the heated calibration filament 3 which migrate to the sensor filament 2. Examples of suitable sodium-bearing compounds for the calibration filament 3 would be sodium silicate or sodium aluminosilicate. The sodium atoms thus generated by the calibration filament 3 strike the heated sensor filament 2 and are converted to positively charged sodium ions. These ions are then attracted to the adjacent ion collector plate 1 which, relative to the filament 2, is at a negative potential and the resulting current flow is a measure of the sodium controllably released by the calibration filament 3.

Figure 2:
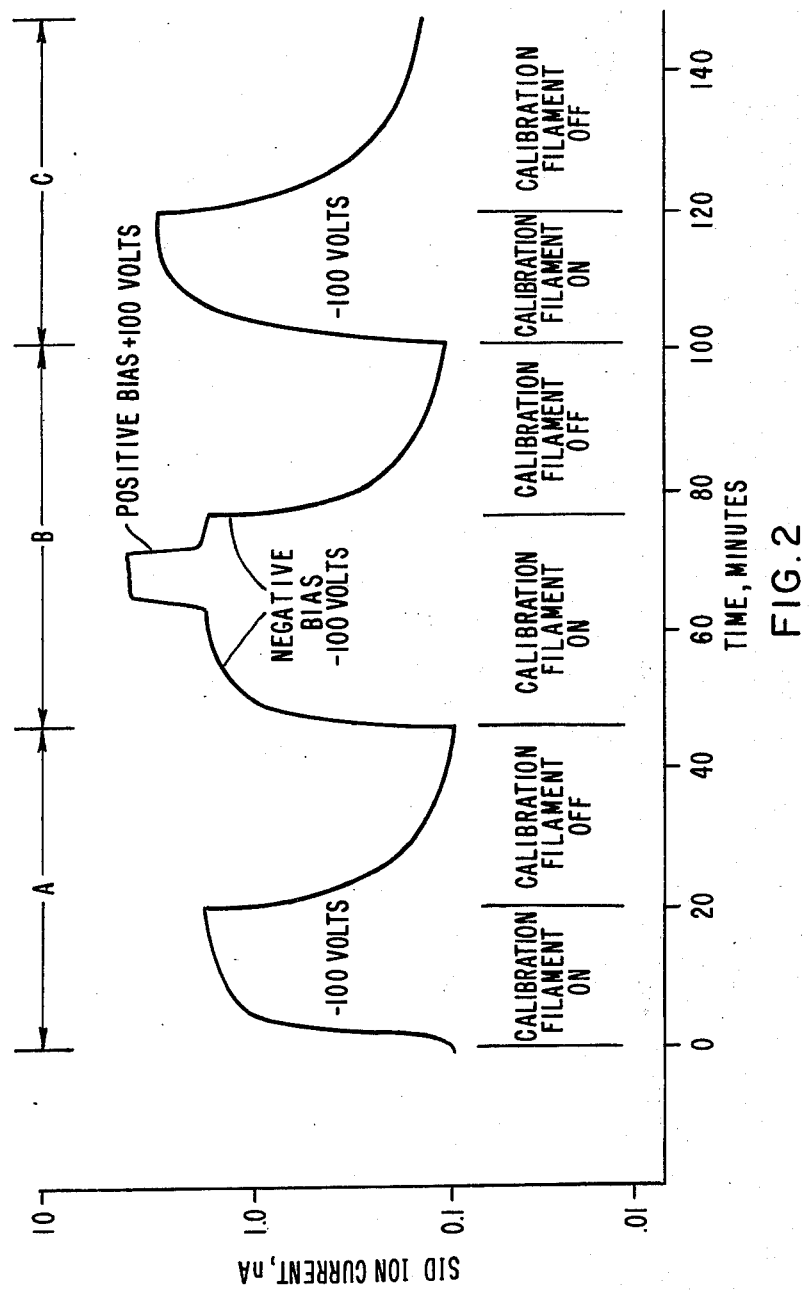

The response of the detector D to the sodium signal thus generated by the calibration filament 3 both with and without the connection of the negative bias voltage source 5 is illustrated in FIG. 2. Section A of the curve was obtained with a negative bias voltage applied to the calibration filament 3. Section B of the curve depicts the response of the detector D to an initial negative bias of the calibration filament 3 with a polarity change to a positive bias and then back again to a negative bias. Section C of the curve illustrates the detector D signal response to the sodium signal of the calibration filament 3 with no bias potential being applied by the bias voltage source 5. The connection and disconnection of the bias voltage source 5 to the calibration filament 3 is illustrated as being achieved by switch 13.

The waveform illustrations of FIG. 3 simulate a calibration procedure with a simultaneous failure of the sensor filament 2. Section A of the waveform illustrates the response of the detector D with no bias potential being applied to the calibration filament 3. Section B of the curve depicts the essentially zero signal response of the detector D with an inoperative sensor filament 2 when the calibration filament 3 is subjective to a negative bias. Section C of the curve illustrates the undesirable condition of an apparent operationally acceptable detector D when the calibration filament 3 has a positive bias potential and the sensor filament 2 is inoperative. This last condition, as illustrated in Section C of the waveform of FIG. 3, of positive bias potential being applied to the calibration filament 3 should therefore be avoided. The loss of negative bias to the collector filament 3 is not as critical however, since, with no bias potential applied to the calibration of filament 3 the generated ion current signal is still below the operating background value of the detector D.

While the activation of the calibration filament 3 has been simply illustrated as being effected by the operation of a switch 10 in a remote control room, the activation of the calibration filament 3 can be controlled by a timed cycle circuit which would avoid inadvertent continuous operation of the calibration filament resulting in reduced operating life of the filament 3.

We claim:

1. In an alkali metal ionization detector having a heated filament electrode for thermally ionizing alkali metal atoms or alkali metal-containing particles in a monitored gas environment to form positive ions, and a source of electrical potential connected to a collector electrode to attract the positive ions and establish an ion current flow which is indicative of the concentration of the alkali metal atoms or alkali metal-containing particles, the improvement for providing the in-situ calibration of the detector, the improvement comprising,
   a calibration filament element including the alkali metal of interest, said element being positioned adjacent to said heated filament electrode, and
   a calibration electrical excitation means connected to said calibration filament element to cause said calibration filament element to generate alkali metal atoms,
   said heated filament electrode responding to said alkali metal atoms by producing positive ions by positive surface ionization, said positive ions being attracted to said collector electrode and establishing a calibration ion current flow in said detector.

2. In a detector as claimed in claim 1, wherein said alkali metal is sodium and said calibration filament element generates sodium atoms in response to said calibration electrical excitation means.

3. In a detector as claimed in claim 2 wherein said calibration filament element thermally volatizes the sodium as neutral sodium atoms in response to said calibration electrical excitation means.

4. In a detector as claimed in claim 1 including a negative electrical bias means connected to said calibration filament element to suppress the emission of positive alkali metal ions from said calibration filament element.

5. In a detector as claimed in claim 1 further including means for periodically activating the generation of alkali metal atoms by said calibration filament element.

* * * * *